(12) United States Patent
Oberg et al.

(10) Patent No.: US 10,669,823 B2
(45) Date of Patent: Jun. 2, 2020

(54) SYSTEM AND METHOD FOR DOWNHOLE IGNITION DETECTION

(71) Applicants: Levi Oberg, Houston, TX (US); Ping Duan, Cypress, TX (US)

(72) Inventors: Levi Oberg, Houston, TX (US); Ping Duan, Cypress, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 461 days.

(21) Appl. No.: 15/338,809

(22) Filed: Oct. 31, 2016

(65) Prior Publication Data

US 2018/0119538 A1    May 3, 2018

(51) Int. Cl.
| E21B 47/00 | (2012.01) |
| --- | --- |
| E21B 47/06 | (2012.01) |
| E21B 43/116 | (2006.01) |
| E21B 43/1185 | (2006.01) |
| G01N 33/00 | (2006.01) |

(52) U.S. Cl.
CPC ........ *E21B 43/11857* (2013.01); *E21B 47/06* (2013.01); *G01N 33/0004* (2013.01)

(58) Field of Classification Search
CPC .......................... E21B 43/267; E21B 43/11857
See application file for complete search history.

(56) References Cited

U.S. PATENT DOCUMENTS

| 3,495,212 A | * | 2/1970 | Brock ............... E21B 43/11857 |
| --- | --- | --- | --- |
| | | | 181/116 |
| 2004/0026086 A1 | | 2/2004 | Patel |
| 2016/0251950 A1 | | 9/2016 | Chen et al. |
| 2017/0321506 A1 | * | 11/2017 | Xu .......................... E21B 43/116 |

FOREIGN PATENT DOCUMENTS

| WO | 2012109711 A1 | 8/2012 |
| --- | --- | --- |
| WO | 2015070297 A1 | 5/2015 |
| WO | 2015148660 A1 | 10/2015 |

OTHER PUBLICATIONS

PCT International Search Report and Written Opinion; International Application No. PCT/US2017/054692 ; International Filing Date: Oct. 2, 2017; dated Jan. 2, 2018; 10 pages.

* cited by examiner

*Primary Examiner* — Robert E Fuller
(74) *Attorney, Agent, or Firm* — Cantor Colburn LLP

(57) ABSTRACT

A system and method for confirming ignition of a fuel source in a wellbore. The system includes a tool, a fuel source associated with the tool, a control unit to ignite the fuel source, and a sensor to receive an ignition parameter corresponding to the fuel source. The ignition parameter indicates that ignition of the fuel source has occurred.

8 Claims, 1 Drawing Sheet

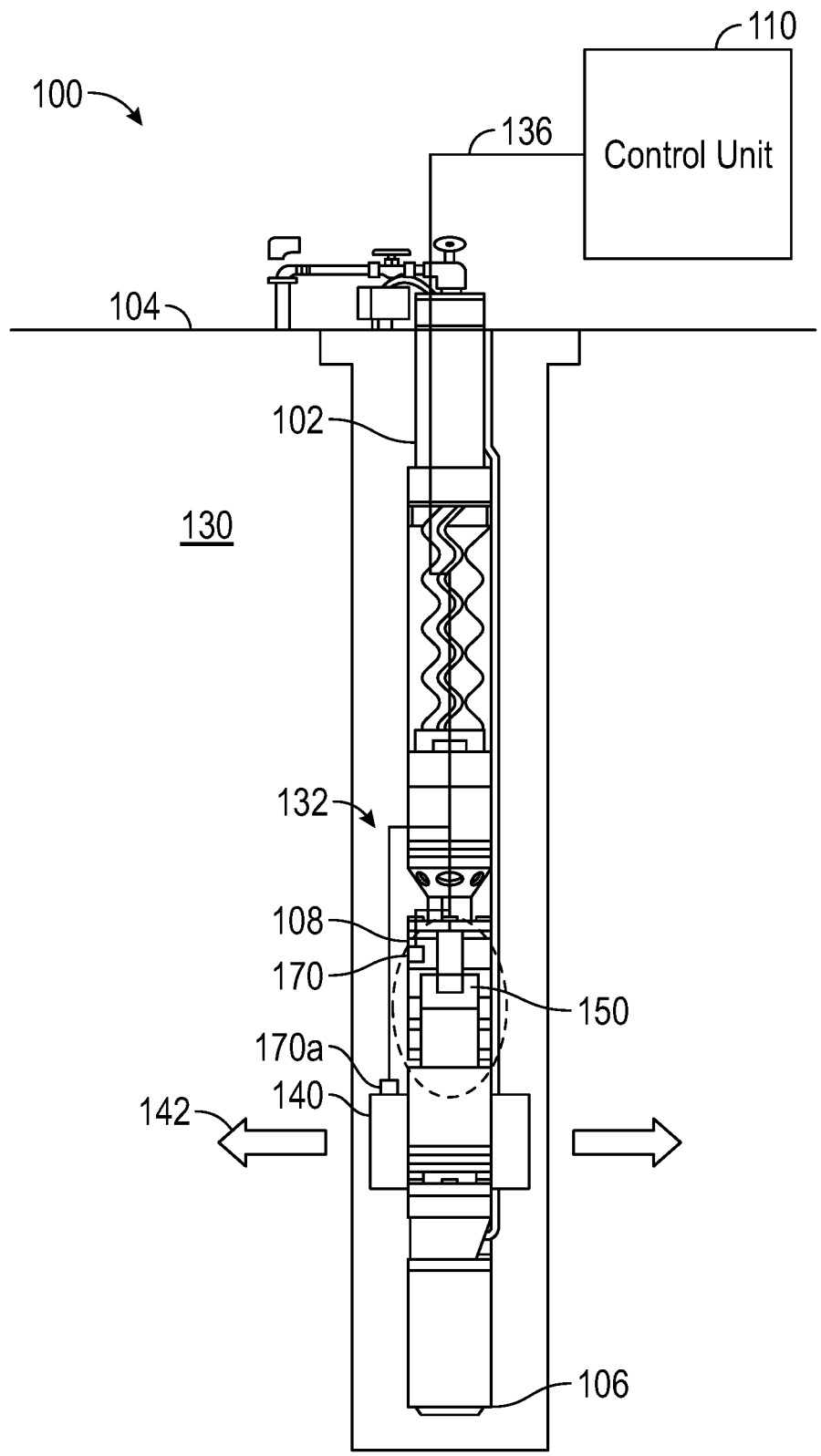

SYSTEM AND METHOD FOR DOWNHOLE IGNITION DETECTION

BACKGROUND

1. Field of the Disclosure

The present invention is related to a system and method of detecting ignition in a wellbore, and in particular, a system and method of detecting ignition of a fuel source for equipment used in a wellbore.

2. Background of the Art

Various downhole operations, such as production, fracturing operations, etc., require downhole fuel sources. In such applications, packers and other setting tools, may be actuated and expanded by combustion of fuel sources. Fuel sources are ignited by remote ignition devices. However, certain ignition devices may not provide confirmation of ignition within the wellbore.

SUMMARY OF THE DISCLOSURE

In one aspect, the present disclosure provides a system for use in a wellbore, the system including a tool, a fuel source associated with the tool, a control unit to ignite the fuel source, and a sensor to receive an ignition parameter.

In another aspect, the present disclosure provides a method for use in a wellbore, the method including: providing a tool at a downhole location within the wellbore, igniting a fuel source associated with the tool via a control unit, and receiving an ignition parameter via a sensor.

Examples of certain features of the apparatus and method disclosed herein are summarized rather broadly in order that the detailed description thereof that follows may be better understood. There are, of course, additional features of the apparatus and method disclosed hereinafter that will form the subject of the claims appended hereto.

BRIEF DESCRIPTION OF THE DRAWINGS

The disclosure herein is best understood with reference to the accompanying figures in which like numerals have generally been assigned to like elements and in which:

FIG. 1 shows a downhole system that includes a tool utilizing an ignition parameter sensor in an exemplary embodiment of the disclosure.

DESCRIPTION OF THE EMBODIMENTS

FIG. 1 shows a downhole system 100 that includes an expanding tool for setting, packing, or other operations of the downhole system 100 in an exemplary embodiment of the disclosure. The downhole system 100 includes a work string 102 disposed in a wellbore 132 formed in a formation 130. The work string 102 extends in the wellbore 132 from a surface location 104 to a downhole location 106. The work string 102 may include a drill string, a production string, a fracturing system including a multi-stage fracturing system, a perforation string, etc. A tool 108 for performing a downhole operation is conveyed to a selected depth of the wellbore by the work string 102. The tool 108 may be a setting tool, a packing tool, a knife or other tool that relies on a downhole fuel source for expansion or general operation, for example.

The tool 108 is schematically illustrated in FIG. 1. The tool 108 may be any tool that expands, sets, separates, or is otherwise actuated by the expansion of combustible gases, such as those provided by the ignition of the fuel source 150. In an exemplary embodiment, the tool 108 is a tool wherein expanding elements 140 move outwardly in an expansion direction 142 when energized by high pressure gasses created by fuel source 150. Tool 108 may be used to prevent flow beyond the position of tool 108, secure another element of string 102 at a certain position at the wellbore 132, chemically cut an element of string 102, etc. In an exemplary embodiment, the fuel source 150 may be ignited to create high temperature and high pressure combustion gasses. In response to these gases, expanding elements 140 of tool 108 may move outwardly in an expansion direction 142 to secure expanding elements 140 towards the outer extents of wellbore 132. In certain embodiments, expanding elements 140 may be compliant elements, while in other embodiments, expanding elements 140 may be rigid elements. Further, expanding elements 140 may be slips or other elements that may expand to create contact with wellbore 132.

The tool 108 may be coupled to a control unit 110 via cable 136. Control unit 110 controls the tool 108 to actuate the tool via igniting the fuel source 150, controlling combustion of a fuel source within the tool, and other functions of the tool. In various embodiments, the control unit 110 may be at a surface location 104 or at a suitable location in the work string 102.

In the illustrated embodiment, the control unit 110 can directly provide an ignition signal to the fuel source 150 to ignite the fuel source 150. In other embodiments, the control until 110 can remotely ignite the fuel source 150 via an intermediate ignition device. In certain embodiments utilizing certain ignition devices, the control unit 110 and/or an operator may not receive confirmation of ignition of the fuel source 150 or proper activation of the tool 108. In the illustrated embodiment, the downhole system 100 includes an ignition parameter sensor 170 to provide relevant ignition parameters to the control unit 110. Advantageously, the ignition parameter sensor 170 can provide confirmation that the fuel source 150 was ignited and/or that the tool 108 was properly activated.

In the illustrated embodiment, the ignition parameter sensor 170 is disposed near the fuel source 150. Further, the ignition parameter sensor 170 is operatively connected to the control unit 110. In certain embodiments, the ignition parameter sensor 170 is connected to the control unit 110 via the control line 136.

In the illustrated embodiment, the ignition parameter sensor 170 can be any suitable sensor to receive ignition parameters. Ignition parameters can be any suitable parameter that can be utilized to indicate that ignition of the fuel source 150 has occurred. In certain embodiments, the ignition parameter sensor 170 is a pressure sensor. In the illustrated embodiment, the ignition parameter sensor 170 is disposed near the fuel source 150 to receive changes in pressure that may indicate successful ignition of the fuel source 150.

In certain embodiments, the ignition parameter sensor 170 is a mechanical pressure switch. In certain embodiments, the mechanical switch can move from a closed position to an open position in response to pressure provided by the ignited fuel source 150.

In certain embodiments, the ignition parameter sensor 170 is a solid state pressure sensor that can utilize a logic circuit or an otherwise embedded system to provide an open circuit or any other suitable signal to the control unit 110 when a pressure threshold is met. In certain embodiments, the ignition parameter sensor 170 can be energized by the control unit 110 in response to attempted ignition of the fuel source 150.

In certain embodiments, the ignition parameter sensor 170 can monitor temperatures within the wellbore or in an area near the fuel source 150. In certain embodiments, the ignition parameter sensor 170 can provide an open circuit or any other suitable signal to the control unit 110 when a temperature threshold is met. In certain embodiments, the temperature threshold can be selected to reflect successful ignition of the fuel source 150.

In certain embodiments, the ignition parameter sensor 170 can monitor current received by the fuel source 150 during ignition. In certain embodiments, the ignition parameter sensor 170 can provide an open circuit or any other suitable signal to the control unit 110 when a current threshold is met. In certain embodiments, the current threshold can be selected to reflect successful ignition of the fuel source 150.

In certain embodiments, the ignition parameter sensor 170 can monitor gases present within the wellbore or near the fuel source 150. In certain embodiments, the ignition parameter sensor 170 can provide an open circuit or any other suitable signal to the control unit 110 when a type of gas, a quantity of gas, or an explosive gas byproduct threshold is met. In certain embodiments, the gas threshold can be selected to reflect successful ignition of the fuel source 150.

In certain embodiments, the ignition parameter sensor 170a can be associated or otherwise affixed to the expanding or moveable elements 140 of the tool 108. In the illustrated embodiment, the ignition parameter sensor 170a can monitor displacement of the expanding elements 140 or any other suitable portion of the tool 108. In certain embodiments, the ignition parameter sensor 170a can provide an open circuit or any other suitable signal to the control unit 110 when a desired movement or displacement threshold is met. In certain embodiments, the position or displacement threshold can be selected to reflect successful ignition of the fuel source 150 and/or successful activation of the tool 108.

Advantageously, the use of the ignition parameter sensor 170,170a allows for the control unit 110 and/or an operator to confirm ignition of the fuel source 150 or actuation of the tool 108. Further, by providing an open circuit signal to the control unit 110, the ignition parameter sensor 170,170a can simulate a "cap break" signal that is provided by certain ignition methods. Use of the ignition parameter sensor 170,170a allows for robust ignition devices that can withstand handling, run-in, and excessive current, while still providing ignition confirmation via a simulated "cap break" signal. Robust ignition methods can allow for reliable ignition of the fuel source 150 and actuation of the tool 108. Further, the ignition parameter sensor 170,170a can further provide ignition confirmation even if multiple ignition attempts are required to ignite the fuel source 150.

Therefore, in one aspect, the present disclosure provides a system for use in a wellbore, the system including a tool, a fuel source associated with the tool, a control unit to ignite the fuel source, and a sensor to receive an ignition parameter corresponding to the fuel source. In various embodiments, the sensor is a pressure sensor. In various embodiments, the pressure sensor is a mechanical switch. In various embodiments, the ignition parameter is a threshold pressure value. In various embodiments, the sensor is a temperature sensor. In various embodiments, the sensor is an ammeter. In various embodiments, the sensor is a gas detector. In various embodiments, the sensor is a displacement sensor associated with the tool. In another aspect, the present disclosure provides a method for use in a wellbore, the method including: providing a tool at a downhole location within the wellbore, igniting a fuel source associated with the tool via a control unit, and receiving an ignition parameter corresponding to the fuel source via a sensor. In various embodiments, the method further includes providing the ignition parameter to the control unit. In various embodiments, the sensor is a pressure sensor. In various embodiments, the pressure sensor is a mechanical switch. In various embodiments, the ignition parameter is a threshold pressure value. In various embodiments, the sensor is a temperature sensor. In various embodiments, the sensor is an ammeter. In various embodiments, the sensor is a gas detector. In various embodiments, the sensor is a displacement sensor associated with the tool.

While the foregoing disclosure is directed to the certain exemplary embodiments of the disclosure, various modifications will be apparent to those skilled in the art. It is intended that all variations within the scope and spirit of the appended claims be embraced by the foregoing disclosure.

What is claimed is:

1. A system for use in a wellbore, comprising:
   a tool;
   a fuel source associated with the tool;
   a control unit to ignite the fuel source; and
   a displacement sensor affixed to an expanding element of the tool, the displacement sensor configured to receive an ignition parameter and send an open circuit signal to the control unit when the ignition parameter indicates that ignition of the fuel source has occurred, wherein the displacement sensor sends the open circuit signal from the displacement sensor to the control unit when a movement of the expanding element meets a displacement threshold.

2. The system of claim 1, further comprising a pressure sensor that is a mechanical switch.

3. The system of claim 1, further comprising an ammeter.

4. The system of claim 1, further comprising a gas detector.

5. A method to confirm ignition within a wellbore, comprising:
   providing a tool at a downhole location within the wellbore;
   igniting a fuel source associated with the tool via a control unit; and
   receiving, at a displacement sensor affixed to an expanding element of the tool, an ignition parameter; and
   sending an open circuit signal from the sensor to the control unit when the ignition parameter indicates that ignition of the fuel source has occurred, wherein the open circuit signal is sent from the sensor to the control unit when a movement of the expanding element meets a displacement threshold.

6. The method of claim 5, further comprising a pressure sensor that is a mechanical switch.

7. The method of claim 5, further comprising an ammeter.

8. The method of claim 5, further comprising a gas detector.

* * * * *